United States Patent
Endo et al.

(10) Patent No.: US 7,659,121 B2
(45) Date of Patent: Feb. 9, 2010

(54) HUMAN SALIVARY GLAND-ORIGIN STEM CELL

(75) Inventors: Fumio Endo, Kumamoto (JP); Kenji Okumura, Kumamoto (JP); Kimitoshi Nakamura, Kumamoto (JP)

(73) Assignee: Bios Research Institute, Inc., Kanagawa (JP)

( * ) Notice: Subject to any disclaimer, the term of this patent is extended or adjusted under 35 U.S.C. 154(b) by 0 days.

(21) Appl. No.: 11/902,018

(22) Filed: Sep. 18, 2007

(65) Prior Publication Data

US 2009/0068734 A1 Mar. 12, 2009

Related U.S. Application Data

(62) Division of application No. 10/546,286, filed as application No. PCT/JP2004/002002 on Feb. 20, 2004, now abandoned.

(30) Foreign Application Priority Data

Feb. 20, 2003 (JP) ............................. 2003-043339

(51) Int. Cl.
*C12N 5/00* (2006.01)
*C12N 15/00* (2006.01)
(52) U.S. Cl. ...................................... 435/455; 435/325
(58) Field of Classification Search ................. 435/455, 435/325
See application file for complete search history.

(56) References Cited

U.S. PATENT DOCUMENTS

2005/0084964 A1 4/2005 Endo et al.

FOREIGN PATENT DOCUMENTS

| JP | 2003-144140 A | 5/2003 |
|---|---|---|
| WO | WO-01/77300 A1 | 10/2001 |
| WO | WO-03/042375 A1 | 5/2003 |

OTHER PUBLICATIONS

Okumura (Hepatology, Jul. 2003, vol. 38, No. 1, p. 104-113).*
Kadoya et al., J. Histochem Cytochem., 1993, vol. 41, No. 11, pp. 1707-1714.
Franchi et al., J. Oral Pathol Med., 1994, vol. 23, No. 10, pp. 457-460.
Azuma et al., Taisha, 1992, No. 29, No. 7, pp. 351-359.
Suzuki et al., Hepatology, 2000, vol. 32, No. 6, pp. 1230-1239.
Okumura et al., Cell Technology, Apr. 2003, vol. 22, No. 5, pp. 534-538.
Azuma et al., Expression of integrin subunits in normal and malignant human salivary gland cell clones and its regulation by transforming growth factor-beta 1, Cancer Letters, 1996, 109, pp. 91-99.
Zulewski, Diabetes, 2001, vol. 50, pp. 521-533.
Assady, Diabetes, Aug. 2001, vol. 50, pp. 1691-1697.
Hisatomi, Hepatology, 2004, vol. 39, pp. 667-675.
Okumura, Hepatology, Jul. 2003, vol. 38, pp. 104-113.
Okumura et al., Am. J. Hum. Gen., Oct. 2001, vol. 69, No. 4, pp. 673.

* cited by examiner

*Primary Examiner*—Michael C. Wilson
(74) *Attorney, Agent, or Firm*—Birch, Stewart, Kolasch & Birch LLP

(57) ABSTRACT

A novel human stem cell which can be differentiated to cells constituting a plurality of human organs including human liver is disclosed. The human stem cell according to the present invention is originated from human salivary gland, which is CD49f-positive, and which can be differentiated to (1) a nestin-positive and albumin-positive cell, (2) an insulin-positive cell and (3) a glucagon-positive cell by culture in vitro.

19 Claims, No Drawings

SEQUENCE LISTING

```
<160> NUMBER OF SEQ ID NOS: 22

<210> SEQ ID NO 1
<211> LENGTH: 24
<212> TYPE: DNA
<213> ORGANISM: Artificial Sequence
<220> FEATURE:
<223> OTHER INFORMATION: Hnf-1alpha forward primer

<400> SEQUENCE: 1
ccagaacctc atcatggcct cact                                          24

<210> SEQ ID NO 2
<211> LENGTH: 24
<212> TYPE: DNA
<213> ORGANISM: Artificial Sequence
<220> FEATURE:
<223> OTHER INFORMATION: Hnf-1alpha reverse primer

<400> SEQUENCE: 2
cacctcgggc ttgtggctgt agag                                          24

<210> SEQ ID NO 3
<211> LENGTH: 21
<212> TYPE: DNA
<213> ORGANISM: Artificial Sequence
<220> FEATURE:
<223> OTHER INFORMATION: Hnf-3alpha forward primer

<400> SEQUENCE: 3
cagcaaacaa aaccacacaa a                                             21

<210> SEQ ID NO 4
<211> LENGTH: 21
<212> TYPE: DNA
<213> ORGANISM: Artificial Sequence
<220> FEATURE:
<223> OTHER INFORMATION: Hnf-3alpha reverse primer

<400> SEQUENCE: 4
taaataaccc tccacaaact a                                             21

<210> SEQ ID NO 5
<211> LENGTH: 20
<212> TYPE: DNA
<213> ORGANISM: Artificial Sequence
<220> FEATURE:
<223> OTHER INFORMATION: Hnf-4alpha forward primer

<400> SEQUENCE: 5
```

-continued gcctacctca aagccatcat 20

<210> SEQ ID NO 6
<211> LENGTH: 20
<212> TYPE: DNA
<213> ORGANISM: Artificial Sequence
<220> FEATURE:
<223> OTHER INFORMATION: Hnf-4alpha reverse primer

<400> SEQUENCE: 6
gaccctccca gcagcatctc 20

<210> SEQ ID NO 7
<211> LENGTH: 20
<212> TYPE: DNA
<213> ORGANISM: Artificial Sequence
<220> FEATURE:
<223> OTHER INFORMATION: Nestin forward primer

<400> SEQUENCE: 7
gcgttggaac agaggttgga 20

<210> SEQ ID NO 8
<211> LENGTH: 20
<212> TYPE: DNA
<213> ORGANISM: Artificial Sequence
<220> FEATURE:
<223> OTHER INFORMATION: Nestin reverse primer

<400> SEQUENCE: 8
tgggagcaaa gatccaagac 20

<210> SEQ ID NO 9
<211> LENGTH: 21
<212> TYPE: DNA
<213> ORGANISM: Artificial Sequence
<220> FEATURE:
<223> OTHER INFORMATION: Pdx-1 forward primer

<400> SEQUENCE: 9
actggattgg cgttgtttgt g 21

<210> SEQ ID NO 10
<211> LENGTH: 22
<212> TYPE: DNA
<213> ORGANISM: Artificial Sequence
<220> FEATURE:
<223> OTHER INFORMATION: Pdx-1reverse primer

<400> SEQUENCE: 10
atgccagagg aagaggagga ct 22

<210> SEQ ID NO 11
<211> LENGTH: 22
<212> TYPE: DNA
<213> ORGANISM: Artificial Sequence
<220> FEATURE:
<223> OTHER INFORMATION: Insulin forward primer

<400> SEQUENCE: 11
agaagaggcc atcaagcaca tc 22

<210> SEQ ID NO 12
<211> LENGTH: 20
<212> TYPE: DNA

```
<213> ORGANISM: Artificial Sequence
<220> FEATURE:
<223> OTHER INFORMATION: Insulin reverse primer

<400> SEQUENCE: 12
gcgggtcttg ggtgtgtaga                                              20

<210> SEQ ID NO 13
<211> LENGTH: 21
<212> TYPE: DNA
<213> ORGANISM: Artificial Sequence
<220> FEATURE:
<223> OTHER INFORMATION: Glut-2 forward primer

<400> SEQUENCE: 13
gtgttccact ggatgaccga a                                            21

<210> SEQ ID NO 14
<211> LENGTH: 22
<212> TYPE: DNA
<213> ORGANISM: Artificial Sequence
<220> FEATURE:
<223> OTHER INFORMATION: Glut-2 reverse primer

<400> SEQUENCE: 14
agaatgatgc agtcattcca cc                                           22

<210> SEQ ID NO 15
<211> LENGTH: 22
<212> TYPE: DNA
<213> ORGANISM: Artificial Sequence
<220> FEATURE:
<223> OTHER INFORMATION: Ngn-3 forward primer

<400> SEQUENCE: 15
taagagcgag ttggcactga gc                                           22

<210> SEQ ID NO 16
<211> LENGTH: 22
<212> TYPE: DNA
<213> ORGANISM: Artificial Sequence
<220> FEATURE:
<223> OTHER INFORMATION: Ngn-3 reverse primer

<400> SEQUENCE: 16
cgtacaagct gtggtccgct at                                           22

<210> SEQ ID NO 17
<211> LENGTH: 20
<212> TYPE: DNA
<213> ORGANISM: Artificial Sequence
<220> FEATURE:
<223> OTHER INFORMATION: Pax-4 forward primer

<400> SEQUENCE: 17
caagtgggaa atgcagctgc                                              20

<210> SEQ ID NO 18
<211> LENGTH: 18
<212> TYPE: DNA
<213> ORGANISM: Artificial Sequence
<220> FEATURE:
<223> OTHER INFORMATION: Pax-4 reverse primer

<400> SEQUENCE: 18
ttccaagcca tacagtag                                                18
```

```
<210> SEQ ID NO 19
<211> LENGTH: 20
<212> TYPE: DNA
<213> ORGANISM: Artificial Sequence
<220> FEATURE:
<223> OTHER INFORMATION: Afp forward primer

<400> SEQUENCE: 19
gttgccaact cagtgaggac                                               20

<210> SEQ ID NO 20
<211> LENGTH: 20
<212> TYPE: DNA
<213> ORGANISM: Artificial Sequence
<220> FEATURE:
<223> OTHER INFORMATION: Afp reverse primer

<400> SEQUENCE: 20
gagcttggca cagatcctta                                               20

<210> SEQ ID NO 21
<211> LENGTH: 21
<212> TYPE: DNA
<213> ORGANISM: Artificial Sequence
<220> FEATURE:
<223> OTHER INFORMATION: Albumin forward primer

<400> SEQUENCE: 21
tcttcctggg catgtttttg t                                             21

<210> SEQ ID NO 22
<211> LENGTH: 20
<212> TYPE: DNA
<213> ORGANISM: Artificial Sequence
<220> FEATURE:
<223> OTHER INFORMATION: Albumin reverse primer

<400> SEQUENCE: 22
aacatttgct gcccactttt                                               20
```

HUMAN SALIVARY GLAND-ORIGIN STEM CELL

This application is a Divisional of application Ser. No. 10/546,286 filed on May 30, 2006 now abandoned and for which priority is claimed under 35 U.S.C. 120. application Ser. No. 10/546,286 is the national phase of PCT International Application No. PCT/JP2004/002002 filed on Feb. 20, 2004 under 35 U.S.C. 371. The entire contents of each of the above-identified applications are hereby incorporated by reference.

TECHNICAL FIELD

The present invention relates to a stem cell originated from human salivary gland.

BACKGROUND ART

Stem cells which are potentially useful for regenerative medicine are now widely studied. Representative stem cells which have been reported include mesenchymal stem cells, neural stem cells, hematopoietic stem cells and pancreatic stem cells.

Mesenchymal stem cells were separated from human adult bone marrow fluid (Pittenger, M. F. et al., Science 284, 143 (1999)). These cells are capable of being differentiated to fat cells, cartilage cells, and bone cells in vitro. As for neural stem cells (Gage, P. H., science 287, 1433-1438 (2000)), separation of neural stem cells from adult central nerve system was first reported in 1992, and separation of stem cells capable of being differentiated to nerve cells, which are originated from adult dermis, was reported (Toma, J. G. et al., Nature Cell Biology, 3, 778-784 (2001)).

Although a number of studies on hematopoietic stem cells have been made, reports on their differentiation functions are relatively new. In 1999, Petersen et al. showed that bone marrow cells are differentiated to hepatic cells (Petersen B. E. et al., Science 284, 1168 (1999)), and in the next year, the fractionated cells obtained by sorting murine hematopoietic cells by c-kit$^{high}$, Thy-1$^{low}$, Lin$^{neg}$ and Sca-1$^+$ are transdifferentiated to stem cells (Lagasse, E. et al., Nature Medicine 6, 1229-1234 (2000)). It is thought that hematopoietic stem cells have transdifferentiation abilities, and differentiation thereof to cardiac muscle (Orlic, D. et al., Nature 410, 701-705 (2001)), as well as to alveolar epithelium, intestine epithelium and skin (Orlic, D. et al., supra), has been reported.

Thus, although studies on the mesenchymal or ectodermal stem cells have been progressed, the number of reports on endodermal stem cells is small. As for human hepatic stem cells, although the existence thereof is thought to be indisputable, there are no reports so far which confirmed the stem cells. As for pancreas, the group of Cornelius et al. separated islet-producing stem cells (IPSCs) from an adult mouse, and reported transplantation experiment of the islet prepared from IPSCs in vitro (Ramiya, V. K. et al., Nature Medicine 6, 278-282 (2000)). Although differentiation of these cells into α, β and δ cells was confirmed, differentiation potential to other cells has not been confirmed. Although it has been reported that the stem cells separated by collection of nestin-positive cells from islet differentiated to cells having a phenotype of endocrine or exocrine of pancreas, and to cells having a phenotype of liver (Zulewski, H. et al., Diabetes 50, 521-533 (2001), immunohistological search by using differentiation markers is not shown.

Induction to hepatic or pancreatic cells from ES cells (embryonic stem cells) has been tried, and differentiation to α or β cells of pancreas can be induced (Lumelsky, N, et al., Science 292, 1389-1394 (2001)). However, induction to human hepatic cells has not been reported.

DISCLOSURE OF THE INVENTION

As described above, a stem cell capable of being differentiated to human hepatic cell has not been obtained. Therefore, a stem cell capable of being differentiated into cells of a plurality of organs including human liver has also not been obtained. In case of using stem cells for regenerative medicine, it is most preferred to transplant cells originated from the patient him/herself in view of preventing the rejection reaction associated in the transplantation. Therefore, if there is a stem cell which can also be prepared from an adult, it is advantageous for regenerative medicine.

An object of the present invention is to provide a stem cell which can be differentiated to a human hepatic cell. Another object of the present invention is to provide a human stem cell which can be differentiated to cells of a plurality of human organs including human liver. A still another object of the present invention is to provide a human stem cell which can be differentiated to a human hepatic cell and which can be prepared also from a human adult.

The present inventors intensively studied to succeed in separating a human stem cell from salivary gland, which can be differentiated to a human nerve cell, a human hepatic cell and to a human pancreatic cell, thereby completing the present invention.

That is, the present invention provides an isolated human stem cell originated from human salivary gland, which is CD49f-positive, and which can be differentiated to (1) a nestin-positive and albumin-positive cell, (2) an insulin-positive cell and (3) a glucagon-positive cell by culture in vitro. The present invention also provides a human stem cell which is nestin-positive and albumin-positive, which is induced by culturing a human salivary gland cell in vitro, and which can be differentiated to an insulin-positive cell and a glucagon-positive cell by culture in vitro. The present invention further provides an insulin-positive cell and a glucagon-positive cell, induced by culturing in vitro the above-described human stem cell according to the present invention. The present invention still further provides a method for obtaining human stem cells, comprising collecting CD49f-positive cells from cells originated from human salivary gland tissue, and culturing the cells in the presence of epidermal growth factor to induce human stem cells originated from human salivary gland, which are CD49f-positive, and which can be differentiated to (1) nestin-positive and albumin-positive cells, (2) insulin-positive cells and (3) glucagon-positive cells by culture in vitro, and collecting the induced human stem cells. The present invention still further provides a method for obtaining human stem cells, comprising culturing in vitro, in the presence of fibroblast growth factor, epidermal growth factor and leukemia inhibitory factor, human stem cells originated from human salivary gland, which are CD49f-positive, and which can be differentiated to (1) nestin-positive and albumin-positive cells, (2) insulin-positive cells and (3) glucagon-positive cells by culture in vitro, to induce nestin-positive and albumin-positive cells, and collecting the induced nestin-positive and albumin-positive cells. The present invention still further provides a method for obtaining insulin-positive cells, comprising culturing in vitro human stem cells which are nestin-positive and albumin-positive, which are induced by culturing human salivary gland cells in vitro, and which can be differentiated to insulin-positive cells and glucagon-positive cells by culture in vitro to induce insulin-positive cells, and collecting the induced insulin-positive cells. The present invention still further provides a method for obtaining glucagon-positive cells, comprising culturing in vitro human stem cells which are nestin-positive and albumin-positive, which are induced by culturing human salivary gland cells in vitro, and which can be differentiated to insulin-positive cells and glucagon-positive cells by culture in vitro to induce glucagon-positive cells, and collecting the induced glucagon-positive cells.

By the present invention, a human stem cell which can be differentiated to cells of a plurality of human organs including human liver was first provided. Since the human stem cell according to the present invention can be differentiated to at least human hepatic cell and to human pancreatic cell, it is useful for regenerative therapies for regenerating human liver and human pancreas. Especially, since the stem cell according to the present invention may be obtained from an adult, it may be recovered from the patient who will receive the regenerative therapy, so that the rejection reaction in transplantation may be avoided, which is very advantageous.

BEST MODE FOR CARRYING OUT THE INVENTION

As will be described in detail in Example below, the human stem cells according to the present invention were obtained by collecting CD49f-positive cells from cells originated from human salivary gland tissue, and culturing the cells in the presence of epidermal growth factor (EGF). The human stem cell according to the present invention can be differentiated to (1) a nestin-positive and albumin-positive cell, (2) an insulin-positive cell and (3) a glucagon-positive cell by culture in vitro (this human stem cell is hereinafter referred to also as "first human stem cell" for convenience). The concentration of EGF during subculture is not restricted and preferably about 5 ng/ml to 80 ng/ml, more preferably about 10 ng/ml to 40 ng/ml, especially preferably about 15 ng/ml to 25 ng/ml. As the culture medium, Williams' E medium or the like, which is conventionally used for culture of human cells, may be employed. CD49f is also called α6 integrin and is a membrane protein which forms a heterodimer with CD29 (β1 integrin). The CD49f in the form of the dimer with CD29 is known as a receptor (VLA-6) of laminin which is an extracellular matrix. In general, it is known to express in T cells, platelets, monocytes, epithelial cells, endothelial cells and in trophoblasts in placenta (Knapp W. et al., eds. Leukocyte Typing IV: White Cell Differentiation Antigens, Oxford University Press, New York. (1989)). In addition, it has been reported that CD49f is expressed in undifferentiated epithelial cells constituting salivary duct primordium during fetal period (Lazowski K W. et al., Differentiation 56: 75-82 (1994)) and in hepatic cells during fetal period (Suzuki A. et al., Hepatology 32, 1230-1239 (2000)).

By culturing the first human stem cell by neurosphere method in the presence of fibroblast growth factor (FGF), epidermal growth factor (EGF) and leukemia inhibitory factor (LIF), a sphere consisting essentially of nestin-positive and albumin-positive cells is formed. The concentration of FGF employed in this method is not restricted and preferably about 5 ng/ml to 80 ng/ml, more preferably about 10 ng/ml to 40 ng/ml, especially preferably about 15 ng/ml to 25 ng/ml. The concentration of EGF is not restricted and preferably about 10 ng/ml to 160 ng/ml, more preferably about 20 ng/ml to 80 ng/ml, especially preferably about 30 ng/ml to 50 ng/ml. The concentration of LIF is not restricted and preferably about 2 ng/ml to 40 ng/ml, more preferably about 5 ng/ml to 20 ng/ml, especially preferably about 7 ng/ml to 15 ng/ml.

This cell can form a spheroid by being cultured by spheroid culture according to a conventional method. As the medium, a medium conventionally used for the culture of human cells, such as Williams' E medium, supplemented with serum such as fetal bovine serum (FBS), is preferred. The concentration of FBS is not restricted, and preferably 5 to 20% by weight, more preferably about 7 to 15% by weight. The outer periphery of the spheroid is constituted by glucagon-positive cells, and the inner side thereof is constituted by insulin-positive cells. The core of the spheroid is insulin-negative and glucagon-negative. By adding 10 mM of glucagon-like peptide-1 (GLP-1) and 5 ng/ml of activin to the differentiation-inducing medium during the spheroid culture, a spheroid lacking the outermost glucagon-positive cells is formed.

Thus, the cells constituting the sphere by the neurosphere method are still human stem cells (this cell is hereinafter referred to also as "second human stem cell" for convenience). The second human stem cell, and in turn, the first human stem cell according to the present invention may be induced to glucagon-positive cell and insulin-positive cell by this method.

Since the stem cell according to the present invention is a human cell, it is preferred to carry out the culture in vitro at 37° C. which is the body temperature of human, and in Example below, the cultures in vitro were carried out at 37° C. unless otherwise specified.

As is well-known, since albumin is a differentiation marker of hepatic cells, the second human stem cell, and in turn, the first human stem according to the present invention, may be differentiated into hepatic cell. Further, since glucagon and insulin are differentiation markers of pancreas, the second human stem cell, and in turn, the first human stem according to the present invention, may be differentiated into a pancreatic cell.

In Example below, the first and the second human stem cells according to the present invention were obtained from an adult. In transplanting cells for regenerative therapy, it is most preferred to transplant the cells of the patient him/herself in view of preventing rejection reaction caused by the transplantation. Since the human stem cells according to the present invention may be obtained from an adult, they may be prepared from the patient him/herself who will receive the transplantation, so that they are very advantageous for transplantation. It should be noted that the human stem cells according to the present invention may be obtained not only from adults, but also from infants.

Since the human stem cells according to the present invention may be differentiated into at least liver and pancreas, regeneration of these human organs may be attained by transplanting the human stem cells according to the present invention. Transplantation of the human stem cells may easily be carried out by infusing a suspension of the human stem cells. The cells may be infused into spleen, the organ to be regenerated or vicinity thereof, or into a vein or the like. The number of the stem cells to be infused is not restricted and may be appropriately selected depending on the symptom, body weight of the patient, administration method and the like, and is usually about 102 to 1010 cells.

EXAMPLE (1) Primary Culture of Salivary Gland Cells

A salivary gland tissue was digested by the following method:

Method for Digesting Salivary Gland Tissue

1. A unilateral submandibular gland (about 2-4 g) enucleated in surgery was minced into pieces sizing 1-2 mm.

2. The minced tissue was transferred to a 50 ml centrifuge tube together with 30 ml of EGTA buffer (containing 8 g of NaCl, 0.4 g of KCl, 69 mg of NaH2PO4, 75 mg of Na2HP04, 2.38 g of HEPES, 0.19 g of EGTA (ethylene glycol tetraacetic acid), 0.35 g of NaHCO3, 0.9 g of glucose and 6 mg of Phenol Red in IL), and shaken by rotation at a rate of 10 rpm at 37° C. for 20 minutes. After the incubation, the minced tissue fluid was centrifuged (100×g, 5 minutes, room temperature), and the supernatant was discarded.

3. The obtained pellet was dispersed in 60 ml of a digestion medium (containing 60 ml of DMEM/F12=1:1, 100 mg of collagenase and 80 mg of hyaluronidase in 60 ml), and the dispersion was transferred to a 50 ml centrifuge tube, followed by shaking the dispersion by rotation at a rate of 10 rpm at 37° C. for 40 minutes. After the incubation, the minced tissue fluid was centrifuged (100×g, 5 minutes, room temperature), and the supernatant was discarded.

4. The obtained pellet was dispersed in 60 ml of a dispersion medium (containing 60 ml of DMEM/F12=1:1, and 80 mg (1000 U/ml)) of dispase in 60 ml), and the dispersion was transferred to a 50 ml centrifuge tube, followed by shaking the dispersion by rotation at a rate of 10 rpm at 37° C. for 60 minutes. During the shaking by rotation, pipetting was performed several times with a 10 ml pipette, thereby mechanically dispersing the minced tissue fluid. After the incubation, the minced tissue fluid was filtered through a cell filter to obtain a cell suspension. The cell suspension was centrifuged (100×g, 5 minutes, 4° C.) to obtain a cell pellet.

5. The cell pellet was suspended in 30 ml of Williams' E medium, and washed three times with the medium.

6. The number of cells was counted, and the rate of living cells was checked. The total number of the cells obtained from 4 g of gland tissue was about 2.0–3.0×107. The rate of living cells was not less than 90%.

Cells were Separated by the Following Method:

Method for Separating Cells (in Case of $1.0 \times 10^7$ Cells)

1. The cells originated from salivary gland, which were collected in (1) described above are resuspended in 0.1% BSA/PBS (500 μl), and incubated (on ice) with an anti-human CD49f monoclonal antibody (clone: GoH3/BD Pharmingen) for 20 minutes. The amount of the antibody used was 1 μg/$1.0 \times 10^6$ cells according to the amount employed in FCM analysis, thereby carrying out labeling.

2. After completion of the labeling, 5 ml of the buffer (same as described above, hereinafter the same buffer is used unless otherwise specified) is added, and the cells are washed and centrifuged.

3. The cell pellet is resuspended in 100 μl of the buffer. To the resultant, goat anti-rat IgG-immobilized microbeads for magnetic cell separation (MACS) are added, and the resultant is incubated (on ice) for 15 minutes after mixing.

4. After washing and centrifuging the cells, the cell pellet is resuspended in 3 ml of buffer.

5. The sample is subjected to cell separation program (POSSEL) of AutoMACS. The cells in CD49f(+) fraction are collected.

6. After washing the collected cells with Williams' E medium, plating was performed. As the culture dish, one coated with type I collagen was used, and as the maintenance medium, Williams' E medium supplemented with 20 ng/ml of recombinant human (rh) EGF, 10% fetal bovine serum (FBS), $10^{-8}$ mol/L insulin, $10^{-6}$ mol/L dexamethasone, 100 U/mL penicillin G, 100 μU/mL of streptomycin was used.

7. By continuing the culture for 2 to 3 weeks, 5 to 7 colonies consisting essentially of fibroblast-like cells are formed. Although most of the cells other than these cells had dropped, they cannot be re-plated and drop during subculture after this step. (This cell is hereinafter referred to as hSGSC (human salivary gland derived stem cell).

8. Cells are harvested from the 100 mm dish after treatment with trypsin-EDTA, and are re-plated (P2) in 2 wells (type I collagen) of a 6-well plate.

(2) Subculturing Method for Short Period (up to P5)

This cell (hSGSC) cannot be subcultured for a long time in the serum-containing medium used for the primary culture. At the time of separation, the cells are in the form of fibroblasts and the cell density on the type I collagen plate is high. However, at P6 or later, most of them are elongated and the mitotic figure observed in a number of cells immediately after the subculture in early stage becomes scarcely observed. Further, as mentioned below, induction of sphere by the neurosphere method becomes impossible. These elongated cells are vimentin-positive and GFAP-positive, and are thought to be immature astrocytes.

To prevent the morphological change and to extend the number of times of the subculture, two points, that is, (1) to keep the cell density at the time of subculture high, and (2) to use a conditioned medium when conducting subculture, were born in mind. The cell density at the time of subculture was kept at not less than $1.0 \times 10^4$ cells/cm$^2$. The conditioned medium diluted 3-fold with the maintenance medium was used in the subculture. Subculturing was performed every 5 to 6 days. By this, not less than 10 passages have been attained up to present.

(3) Method for Inducing Insulin-Producing Cells Using Cells Originated from Salivary Gland This cell formed a spherical cell cluster by being cultured in a serum-free medium containing bFGF, rhEGF and rhLIF according to the neurosphere method. More concretely, the neurosphere method was carried out as follows: In a medium composition (Neurobasal medium (Invitrogen) containing 2% B-27 additives (Invitrogen), 1% N-2 additives (Invitrogen), 20 ng/ml basic fibroblast growth factor (R & D) and 10 ng/ml recombinant human leukemia inhibitory factor (Chemicon), hSGSC cells were suspended, and plated on a poly-D-lysine-coated dish (Phalcon). The number of cells was about 2–3×$10^5$ cells per a 60 mm dish. The medium was replaced every other day and half amount of bFGF was supplemented on the day between the replacement of the medium. The hSGSC cells adhere to the surface of the dish for several days from the plating, they gradually aggregate. After being detached from the dish surface, the cells proliferate in the suspended state. These cell clusters are mostly composed of nestin-positive cells, which is a marker of neural stem cells. When differentiation was induced in a serum-containing medium, emergence of Tuj-1-positive cells, GFAP-positive cells and GalC-positive cells, respectively, was confirmed. From these result, it was thought that the cells had a potency of precursor cells of neural stem cells.

The hSGSC cells prepared from the salivary gland were subjected to spheroid culture. Spheroid 96U Plate (96-well plate) of SUMITOMO BAKELITE CO., LTD. was used. As the medium, Williams' E medium supplemented with GLP-1 was used. The cells were plated at a cell density of $3.0 \times 10^3$ cells/well.

Immediately after the beginning of the spheroid culture, hSGSC cells were in the form of single cells, but they started aggregation within two hours, and a completely single spheroid was formed after 12 hours. (Although cells (large vacuolar cells) other than hSGSC cells may contaminate when plating, the cells other than hSGSC cells are not incorporated into the spheroid.)

Seven days after the beginning of the culture, the spheroids were subjected to immunofluorescent staining with anti-insulin, anti-glucagon and anti-GFAP antibodies. As a result, the outer periphery of the spheroid consisted essentially of glucagon-positive cells, and the core of the spheroid consisted essentially of insulin-positive cells.

RNAs were recovered from the spheroids and RT-PCR was performed. Primers were designed for PDX-1, ngn-3, Glut-2, PAX-4 and insulin, respectively, and PCR was performed. As a result, expressions of PDX-1, ngn-3, Glut-2 and insulin were confirmed. Expression of PAX-4 was not observed. The nucleotide sequences of the primer sets used for the RT-PCR were as follows:

Hnf-1alpha (328 bp),
forward
5'-ccagaacctcatcatggcctcact-3'    (SEQ ID NO: 1)
and reverse
5'-cacctcgggcttgtggctgtagag-3';   (SEQ ID NO: 2)

Hnf-3alpha (290 bp),
forward
5'-cagcaaacaaaaccacacaaa-3'       (SEQ ID NO: 3)
and reverse
5'-taaataaccctccacaaacta-3';      (SEQ ID NO: 4)

Hnf-4alpha (275 bp),
forward
5'-gcctacctcaaagccatcat-3'        (SEQ ID NO: 5)
and reverse
5'-gaccctcccagcagcatctc-3';       (SEQ ID NO: 6)

Nestin (327 bp),
forward
5'-gcgttggaacagaggttgga-3'        (SEQ ID NO: 7)
and reverse
5'-tgggagcaaagatccaagac-3';       (SEQ ID NO: 8)

Pdx-1 (303 bp),
forward
5'-actggattggcgttgtttgtg-3'       (SEQ ID NO: 9)
and reverse
5'-atgccagaggaagaggaggact-3';     (SEQ ID NO: 10)

Insulin (200 bp),
forward
5'-agaagaggccatcaagcacatc-3'      (SEQ ID NO: 11)
and reverse
5'-gcgggtcttgggtgtgtaga-3';       (SEQ ID NO: 12)

Glut-2 (200 bp),
forward
5'-gtgttccactggatgaccgaa-3'       (SEQ ID NO: 13)
and reverse
5'-agaatgatgcagtcattccacc-3';     (SEQ ID NO: 14)

Ngn-3 (230 bp),
forward
5'-taagagcgagttggcactgagc-3'      (SEQ ID NO: 15)
and reverse
5'-cgtacaagctgtggtccgctat-3';     (SEQ ID NO: 16)

Pax-4 (361 bp),
forward
5'-caagtgggaaatgcagctgc-3'        (SEQ ID NO: 17)
and reverse
5'-ttccaagccatacagtag-3';         (SEQ ID NO: 18)

Afp (240 bp),
forward
5'-gttgccaactcagtgaggac-3'        (SEQ ID NO: 19)
and reverse
5'-gagcttggcacagatcctta-3';       (SEQ ID NO: 20)

Albumin (339 bp),
forward
5'-tcttcctgggcatgtttttgt-3'       (SEQ ID NO: 21)
and reverse
5'-aacatttgctgcccactttt-3';       (SEQ ID NO: 22)

(4) Induction of Sphere Formation in Serum-Free Medium and Induction of Albumin-Positive Cells, Using Cells Originated from Salivary Gland As mentioned above, hSGSC forms a sphere like neurosphere, which consists essentially of nestin-positive cells by neurosphere method. The neurosphere method was repeated except that FGF-2 (basic FGF) contained in the medium was replaced with FGF-4, and a similar sphere was formed. These spheres (F2 sphere and F4 sphere) were subjected to RT-PCR (described above) for nestin, and the result was nestin-positive. Expressions of HNF-3a and AFP were simultaneously confirmed. Expression of albumin was also confirmed. In these spheres, expressions of PDX-1, ngn-3, Glut-2, PAX-4, insulin and the like were not observed at all. The profile of RT-PCR is shown in Table 1 below.

TABLE 1

|  | F2 sphere | F4 sphere | HOE44/d7 | G(+)/d7 | G(+)/d3 | HepG2 |
|---|---|---|---|---|---|---|
| PDX1 | ± | − | − | + | + | − |
| ngn3 | − | − | + | 2+ | + | − |
| PAX4 | − | − | − | − | − |  |
| Glut.2 | − | − | + | + | + |  |
| Insulin | − | − | + | 2+ | + |  |
| Glucagon | − | − | − | − | − |  |
| AFP | 2+ | 2+ | 2+ | 2+ | 2+ | 2+ |
| Albumin | + | + | ± | ± | ± | 2+ |
| Nestin | + | + | ± |  | ± | + |
| HNF1a | − | − |  |  | − | + |
| HNF3a | + | + |  |  | + | + |
| HNF4a | − | − |  |  | − | 2+ |

Although HNF-3a is expressed only in endothelial tissue in adults, it is known to be expressed also in early neural tissue and in notochord (mesoblast) in E8-E9. Also from the fact that neural marker-positive cells may be induced from F2 sphere, hSGSC is thought to be a bipotent stem cell retaining an embryonic character.

In this Example, the markers expressed by the cells were examined by immunocytostaining or flow cytometry. All of the fluorescence-labeled antibodies used for staining were commercially available, and the protocols of the methods were in accordance with the instructions attached to the commercially available fluorescence-labeled antibodies or the commercially available flow cytometry apparatus. That is, immunocytostaining was carried out in accordance with immunohisto/cytostaining Guide from DAKO. Flow cytometry was carried out in accordance with the Flow Cytometry Protocol by BD PHARMINGEN. The used antibodies are listed below.

Anti-Human CD49f Monoclonal Antibody (Clone: GoH3/Pharmingen)
Anti-GalC antibody (Sigma)
Anti-GFAP antibody (DAKO/Chemicon)
Anti-glucagon antibody (DAKO)
Anti-insulin antibody (Biogenesis)
Anti-human nestin antibody (Chemicon)
Anti-Tuj-1 antibody (RMD)

INDUSTRIAL AVAILABILITY

Since the human stem cell according to the present invention can be differentiated to at least human hepatic cell and to human pancreatic cell, it is useful for regenerative therapies for regenerating human liver and human pancreas. Especially, since the stem cell according to the present invention may be obtained from an adult, it may be recovered from the patient who will receive the regenerative therapy, so that the rejection reaction in transplantation may be avoided, which is very advantageous.

The invention claimed is:

1. A method for obtaining insulin-positive cells, comprising:
   culturing human salivary gland cells in vitro to obtain human stem cells which are nestin-positive and albumin-positive;
   differentiating said human stem cells which are nestin-positive and albumin-positive by culture in vitro to induce insulin-positive cells, and collecting the induced insulin-positive cells.

2. A method for obtaining glucagon-positive cells, comprising:
   culturing human salivary gland cells in vitro to obtain human stem cells which are nestin-positive and albumin-positive;
   differentiating said human stem cells which are nestin-positive and albumin-positive by culture in vitro to induce glucagon-positive cells, and collecting the induced glucagon-positive cells.

3. The method according to claim 1, wherein said culturing is performed in the presence of fibroblast growth factor, epidermal growth factor and leukemia inhibitory factor.

4. The method according to claim 1, wherein said cells obtained from human salivary gland tissue are CD49f-positive.

5. The method according to claim 1, wherein said human stem cells are differentiated into human hepatic cells or human pancreatic cells.

6. The method according to claim 5, wherein said human stem cells are differentiated into human hepatic cells.

7. The method according to claim 5, wherein said human stem cells are differentiated into human pancreatic cells.

8. The method according to claim 1, wherein said cells from salivary gland tissue are obtained from an adult.

9. The method according to claim 1, wherein said cells from salivary gland tissue are obtained from an infant.

10. The method according to claim 1 or claim 2, wherein said culturing in vitro is carried out by spheroid culture.

11. The method according to claim 2, wherein said culturing is performed in the presence of fibroblast growth factor, epidermal growth factor and leukemia inhibitory factor.

12. The method according to claim 2, wherein said cells obtained from human salivary gland tissue are CD49f-positive.

13. The method according to claim 2, wherein said human stem cells are differentiated into human hepatic cells or human pancreatic cells.

14. The method according to claim 13, wherein said human stem cells are differentiated into human hepatic cells.

15. The method according to claim 13, wherein said human stem cells are differentiated into human pancreatic cells.

16. The method according to claim 2, wherein said cells from salivary gland tissue are obtained from an adult.

17. The method according to claim 2, wherein said cells from salivary gland tissue are obtained from an infant.

18. A method for obtaining insulin-positive cells, comprising:
   culturing CD49f-positive human salivary gland cells in vitro in the presence of epidermal growth factor to obtain human stem cells which are nestin-positive and albumin-positive;
   differentiating said human stem cells which are nestin-positive and albumin-positive by spheroid culture in vitro in the presence of epidermal growth factor, fibroblast growth factor and leukemia inhibitory factor to induce insulin-positive cells; and
   collecting the induced insulin-positive cells.

19. A method for obtaining glucagon-positive cells, comprising:
   culturing CD49f-positive human salivary gland cells in vitro in the presence of epidermal growth factor to obtain human stem cells which are nestin-positive and albumin-positive;
   differentiating said human stem cells which are nestin-positive and albumin-positive by spheroid culture in vitro in the presence of epidermal growth factor, fibroblast growth factor and leukemia inhibitory factor to induce glucagon-positive cells; and
   collecting the induced glucagon-positive cells.

* * * * *